(12) United States Patent
Letinois et al.

(10) Patent No.: US 11,724,996 B2
(45) Date of Patent: Aug. 15, 2023

(54) SYNTHESIS OF INTERMEDIATES FOR THE PREPARATION OF ALPHA-TOCOPHEROL

(71) Applicant: DSM IP Assets B.V., Heerlen (NL)

(72) Inventors: Ulla Letinois, Kaiseraugst (CH);
Thomas Netscher, Kaiseraugst (CH);
August Ruettimann, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 179 days.

(21) Appl. No.: 17/306,886

(22) Filed: May 3, 2021

(65) Prior Publication Data

US 2021/0300886 A1 Sep. 30, 2021

Related U.S. Application Data

(62) Division of application No. 16/630,218, filed as application No. PCT/EP2018/068821 on Jul. 11, 2018, now abandoned.

(30) Foreign Application Priority Data

Jul. 12, 2017 (EP) ..................... 17180880

(51) Int. Cl.
| | |
|---|---|
| C07D 311/72 | (2006.01) |
| C07C 45/29 | (2006.01) |
| C07C 45/61 | (2006.01) |
| C07D 311/22 | (2006.01) |

(52) U.S. Cl.
CPC ............ *C07D 311/72* (2013.01); *C07C 45/29* (2013.01); *C07C 45/298* (2013.01); *C07C 45/61* (2013.01); *C07D 311/22* (2013.01)

(58) Field of Classification Search
CPC ....... C07C 45/29; C07C 45/298; C07C 45/61; C07D 311/22
See application file for complete search history.

(56) References Cited

U.S. PATENT DOCUMENTS

| 11,078,178 B2 * | 8/2021 | Beumer | ................ C07C 33/042 |
| 2020/0190051 A1 | 6/2020 | Beumer | |

FOREIGN PATENT DOCUMENTS

| CN | 1249306 | 4/2000 |
| CN | 6199356 | 11/2005 |
| EP | 1 446 398 | 8/2004 |
| WO | 2005/054223 | 6/2005 |
| WO | 2014/096066 | 6/2014 |
| WO | 2015/001027 | 1/2015 |

OTHER PUBLICATIONS

Ali; Synthetic Communications 2006, 36, 1751-1759. https://doi.org/10.1080/00397910600616859 (Year: 2006).*
Hormi; Tetrahedron 1998, 54, 1943-1952. https://doi.org/10.1016/S0040-4020(97)10409-4 (Year: 1998).*
International Search Report for PCT/EP2018/068821, dated Sep. 3, 2018, 3 pages.
Written Opinion of the ISA for PCT/EP2018/068821, dated Sep. 3, 2018, 5 pages.
Chapelat, Julien (2009). Asymetric synthesis of 2,2-disubstituted chromanols—Novel approaches to Vitamin E analogues (Doctoral dissertation, University of Basel, Basel, Switzerland), 176 pages. Downloaded Jul. 24, 2020 from http://edoc.unibas.ch/diss/DissB_8851 (doi: 10.5451/unibas-005005974) (Year: 2009).
Kamal-Eldin; Lipids 31, 1996, 671-701. doi: 10.1007/BF02522884 (Year: 1996).
Hua; Org. Lett. 2003, 5, 21, 3831-3834 with supporting information, 15 pages. (Year: 2003).
Christopher Cox et al., "*Concise Synthesis of Lactonamycin Model System by Diastereoselective Dihydroxylation of a Highly Functionalized Napthoquinone*", Organic Letters, 2001, vol. 3, No. 18, 2899-2902.
Julien Chapelat, "*Asymmetric synthesis of 2,2-disubstituted chromanols—Novel approaches to Vitamin E analogues*", Dissertation for Doctor of Philosophy, University of Basel, 2009.

* cited by examiner

*Primary Examiner* — Daniel R Carcanague (74) *Attorney, Agent, or Firm* — Nixon & Vanderhye P.C.

(57) ABSTRACT

The present invention relates to a novel synthetic pathway for alpha-tocopherol. The invention discloses different reactions yielding some new intermediates in a very high yield and stereoselectivity.

10 Claims, 3 Drawing Sheets

SYNTHESIS OF INTERMEDIATES FOR THE PREPARATION OF ALPHA-TOCOPHEROL

CROSS-REFERENCE TO RELATED APPLICATIONS

This application is a divisional of U.S. application Ser. No. 16/630,218 filed on 10 Jan. 2020 (now abandoned), which in turn is the U.S. national phase of International Application No. PCT/EP2018/068821 filed 11 Jul. 2018, which designated the U.S. and claims priority to EP Patent Application No. 17180880.1 filed 12 Jul. 2017, the entire contents of each of which are hereby incorporated by reference.

TECHNICAL FIELD

The present invention relates to a novel synthesis of alpha-tocopherol, or of intermediates to its synthesis.

BACKGROUND OF THE INVENTION

α-Tocopherol is a very important compound in the field of food and feed. A variety of routes for its synthesis exist. As all syntheses are rather complex and comprise a very large number of reaction steps, a big interest exists in new synthetic pathways.

α-Tocopherol is part of natural vitamin E. It has been shown that tocopherols having the R-configuration at the chiral centre situated next to the ether atom in the ring of the molecule (indicated by # in the formulas used later on in the present document) (i.e. 2R-configuration) have in general higher bioactivity (biopotency), as compared to the corresponding isomers having S-configuration. Particularly active are the isomers of tocopherols having the natural configuration at all chiral centres as disclosed for example by H. Weiser et al. in *J. Nutr.* 1996, 126(10), 2539-49. Hence, there exists a very big interest in new synthetic pathways for α-tocopherol in general, for (2R)-α-tocopherol in particular, and most particularly for (2R,4'R,8'R)-α-tocopherol. As to keep flexibility in the present but particular in future tocopherol production, there exist also a major interest in new synthetic pathway leading using different starting products and intermediates.

SUMMARY OF THE INVENTION

Therefore, the problem to be solved by the present invention is to offer a new process for the preparation of α-tocopherol in general, for (2R)-α-tocopherol in particular, and most particularly for (2R,4'R,8'R)-α-tocopherol, respectively for intermediates for the synthesis thereof.

This problem has been surprisingly solved by a new synthetic pathway. The individual steps have a remarkably high yield and selectivity and stereoselectivity. Furthermore, it has been found that a step involving a cyclization reaction can be used to get a high stereoselectivity to yield a desired isomer of α-tocopherol. Therefore, it is possible to obtain at high yield and stereoselectivity (2R)-α-tocopherol, or (2R, 4'R,8'R)-α-tocopherol, respectively.

Further aspects of the invention are subject of further independent claims. Particularly preferred embodiments are subject of dependent claims.

DETAILED DESCRIPTION OF THE INVENTION

The present invention offers a new synthesis of α-tocopherol respectively some new intermediates.

Figure 1:
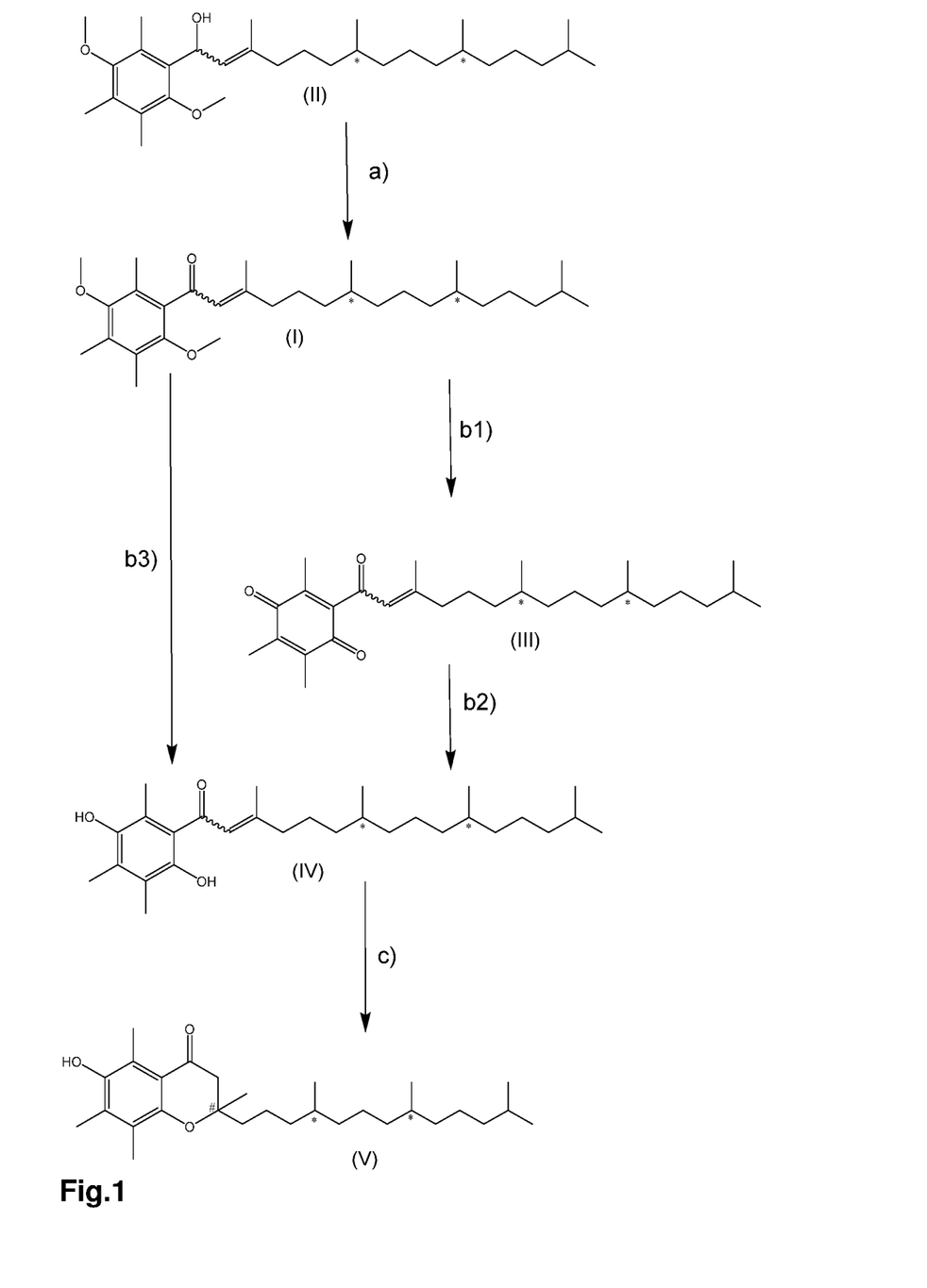
FIG. 1 schematically show a synthesis pathway a) for forming a compound of formula (I) from a compound of formula (II); a synthesis pathway b1) for forming a compound of formula (III) from a compound of formula (I); a synthesis pathway b2) for forming a compound of formula (IV) for a compound of formula (III); a synthesis pathway b3) for forming a compound of formula (IV) from a compound of formula (I and a synthesis pathway c) for forming a compound of formula (V) from a compound of formula (IV)
Figure 2:
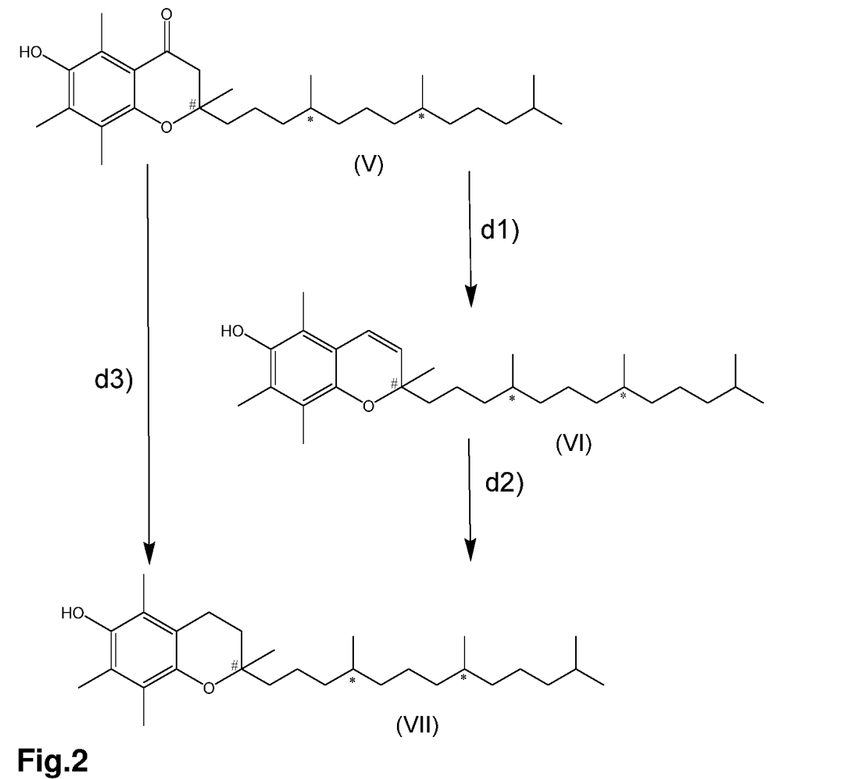
FIG. 2 and 2a schematically show synthesis pathways for chemically transforming compounds of formula (V) and formula (V-R) to compound of formula (VII) and formula (VII-R), respectively.
Figure 2A:
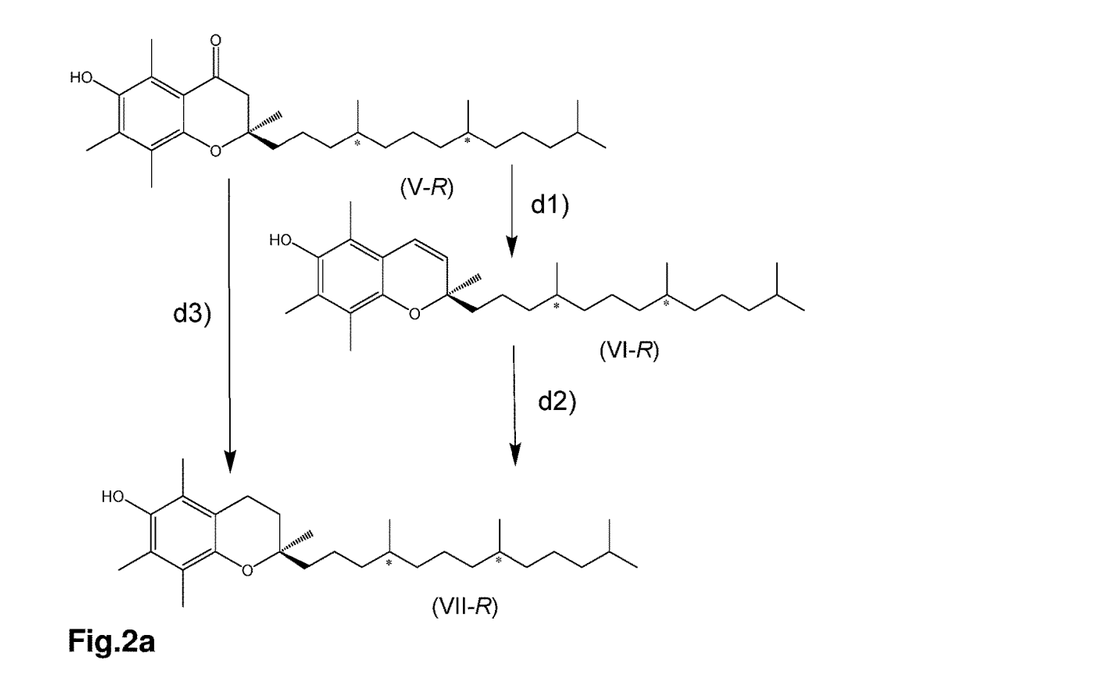

FIGS. 1, 2, 2a, 3 and 4 show schematically the synthetic pathways related to this synthesis:

Compound of formula (II) is oxidized in a reaction step a) to compound of formula (I). Compound of formula (I) can be either transferred directly (i.e. in a one-step reaction) to compound of formula (IV) by the reaction b3) or in a two-step reaction via intermediate of compound of formula (III) by the reaction b1) followed by the reaction b2). Compound of formula (IV) is transformed to compound of formula (V) by a cyclization reaction (step c). Compound of formula (V) can then be transformed to α-tocopherol either directly (i.e. in a one-step reaction) by the reaction d3) or in a two-step reaction via intermediate of compound of formula (VI) by the reaction d1) followed by the reaction d2).

Details on the different reactions and processes are discussed in detail in the following.

Therefore, in a first aspect, the present invention relates to a process of manufacturing a compound of formula (I) from a compound of formula (II)

using an oxidizing agent which is capable of oxidizing a secondary hydroxyl group in the presence of an olefinic C═C double bond to a keto group without modifying said olefinic C—C group;

wherein the wavy line represents a carbon-carbon bond which is linked to the adjacent carbon-carbon double bond so as to have said carbon-carbon double bond either in the Z- or in the E-configuration and
* represents a chiral center.

This process is schematically shown in FIG. 1 as reaction a).

A "$C_{x-y}$-alkyl" group is an alkyl group comprising x to y carbon atoms, i.e., for example, a $C_{1-3}$-alkyl group is an alkyl group comprising 1 to 3 carbon atoms. The alkyl group can be linear or branched. For example —$CH(CH_3)$—$CH_2$—$CH_3$ is considered as a $C_4$-alkyl group.

In case identical labels for symbols or groups are present in several formulae, in the present document, the definition of said group or symbol made in the context of one specific formula applies also to other formulae which comprises said same label.

The expression "process of preparation" is a synonym for "method of preparation" and can be used interchangeable to each other.

The chirality of an individual chiral carbon centre is indicated by the label R or S according to the rules defined by R. S. Cahn, C. K. Ingold and V. Prelog. This R/S-concept and rules for the determination of the absolute configuration in stereochemistry is known to the person skilled in the art.

"Constitutional isomers" are isomers having the same molecular formula but the atoms are differently linked together. For example, n-pentane, iso-pentane, neo-pentane are constitutional isomers of pentane, or 1,1-dichloro-2-methyl-propane, 2,3-dichlorobutane or 1,2-dichlorobutane, respectively, are (a few of all) constitutional isomers of dichlorobutane.

In the present document, any dotted line in formulae represents the bond by which a substituent is bound to the rest of a molecule.

Any wavy line in any formula of this document represents a carbon-carbon bond which is linked to an adjacent carbon-carbon double bond so as to have said carbon-carbon double bond either in the Z- or in the E-configuration. In other words, a formula having a wavy line represents a formula covering the E as well as the Z isomer.

* and # in any formula of this document represents a chiral (carbon) center.

The hydroxyl group in formula (II) is oxidized in the above reaction to a ketone group in formula (I).

It is important to note that by the reactions of FIGS. 1 and 2 and 2a described hereafter, the configuration at the chiral centers marked by * in the respective formulae is not changed by these reactions.

It is preferred, that the double bond to which the carbon-carbon bond represented by a wavy line in any of the formulae of this document is in the E-configuration, particularly of formula (I), (II), (III) or (IV), is in the E-configuration.

It is preferred that the chiral centers, preferably all the chiral centers, indicated by * in the formulae of this document, particularly in the formula (I), (III) or (IV), are in the R-configuration.

The oxidizing agent is preferably $MnO_2$. It has turned out that $MnO_2$ is particularly well suited for the oxidation of compound of formula (II) to the compound of formula (I). Preferably the $MnO_2$ is prepared by precipitation, i.e. the manganese (IV) oxide is preferably a so-called precipitated or active $MnO_2$.

Furthermore, it is advantageous, that the oxidation is performed in an organic solvent, preferably in a hydrocarbon, particularly an aliphatic hydrocarbon, preferably in an aliphatic hydrocarbon selected from the group consisting of pentane, hexane, heptane and cyclohexane, as well as their constitutional isomers, or in a halogenated hydrocarbon, particularly in a halogenated hydrocarbon selected from the group consisting of chlorinated methane, ethane, propane, butane and pentane as well as their constitutional isomers. Preferably the halogenated hydrocarbons comprise more than 1 halogen atom. Preferred halogenated hydrocarbon is dichloromethane. The hydrocarbons are preferred in comparison to the halogenated hydrocarbons.

Most preferred organic solvent is hexane.

The oxidation generally is performed at a temperature of between 10° C. and 60° C., particularly at room temperature (23° C.).

The oxidation is preferably performed under inert atmosphere, such as nitrogen or argon.

It is preferred to use a significant molar excess of the respective oxidizing agent, preferably $MnO_2$, relative to compound of formula (II). It is preferred that the molar ratio of the respective oxidizing agent to compound of formula (II), particularly of $MnO_2$ to the compound of formula (II), is between 10 and 100, particularly between 30 and 65.

Compound of formula (I) can be purified by suitable methods. Particularly useful is purification by chromatography using silica as stationary phase.

Figure 3:
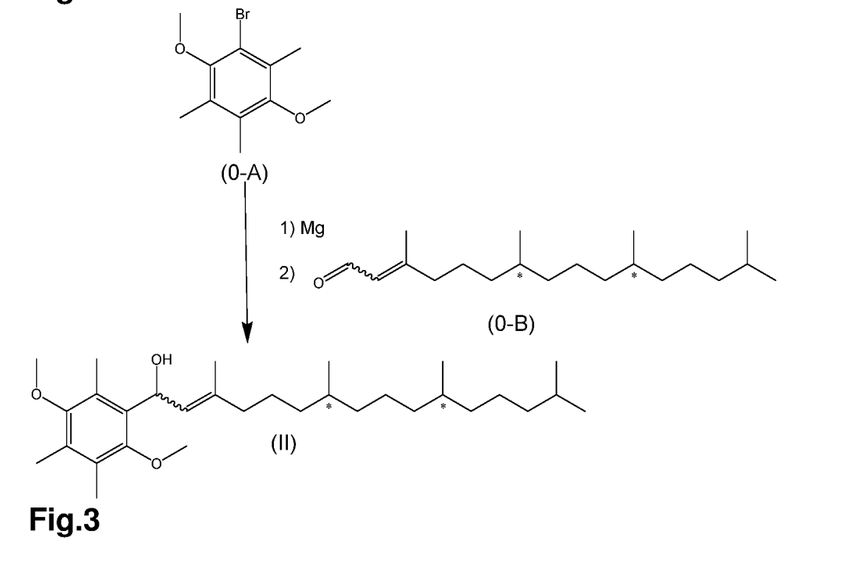
FIG. 3 schematically shows a synthesis process for forming a compound of formula (II)

The starting product for the above oxidation reaction can be obtained by reaction as schematically shown in FIG. 3.

1-bromo-2,5-dimethoxy-3,4,6-trimethylbenzene [formula (0-A)] is first transformed to the respective Grignard reagent using magnesium, which then is added to the 3,7,11,15-tetramethylhexadec-2-enal [formula (0-B)] to form compound of formula (II).

Preferably (E,R,R)-phytal (=(2E,7R,11R)-3,7,11,15-tetramethylhexadec-2-enal) [formula (0-B-ERR)] is used as compound of formula (0-B), which then leads to the preferred staring material of formula (II), (2'E,7'R,11'R)-1-(2,5-di-methoxy-3,4,6-trimethylphenyl)-3,7,11,15-tetramethylhexadec-2-en-1-ol [formula (II-ERR)].

Phytal can be obtain from phytol, as (E,R,R)-phytal from (E,R,R)-phytol, by oxidation in a method known by the person skilled in the art.

1-bromo-2,5-dimethoxy-3,4,6-trimethylbenzene can be obtained by the reaction of 1,4-dimethoxy-2,3,5-trimethylbenzene with bromine (Br$_2$).

Using (2'E,7'R,11'R)-1-(2,5-dimethoxy-3,4,6-trimethylphenyl)-3,7,11,15-tetramethylhexadec-2-en-1-ol [formula (II-ERR)] as starting material for the above oxidation, (2'E,7'R,11'R)-1-(2,5-dimethoxy-3,4,6-trimethylphenyl)-3,7,11,15-tetramethylhexadec-2-en-1-one (I-ERR), as preferred embodiment of compound of formula (I), is formed.

(I-ERR)

In a further aspect, the present invention relates to a process of manufacturing a compound of formula (III) from a compound of formula (I)

(III)

(I)

by an oxidative demethylation using a Ce(IV) salt or a Fe(III) salt, preferably selected from the group consisting of Ce(NH$_4$)$_2$(NO$_3$)$_6$, Ce(SO$_4$)$_2$, FeCl$_3$ and their respective hydrates, most preferably Ce(NH$_4$)$_2$(NO$_3$)$_6$;

This process is schematically shown in FIG. 1 as reaction b1).

Typically, this reaction [b1)] occurs in the presence of acetic acid. Furthermore, it is advantageous, that the reaction is performed in an organic solvent, preferably in a hydrocarbon, particularly an aromatic hydrocarbon, preferably in toluene.

It is preferred that this reaction occurs in an organic solvent in the presences of water. Particularly, the reaction occurs in the presence of water and acetonitrile and optionally a further organic solvent.

Due to the exothermic reaction, it is preferred to add the oxidizing agent slowly under cooling conditions (reaction temperature lower than 10° C., preferably lower than 5° C.) and intense stirring.

The oxidation is preferably performed under inert atmosphere, such as nitrogen or argon.

It is preferred to use a molar excess of the respective oxidizing agent, particularly of the Ce(IV) salt, relative to the compound of formula (I). It is preferred that the molar ratio of the respective oxidizing agent to the compound of formula (I), particularly of the Ce(IV) salt to the compound of formula (I), is between 1.5 and 10, particularly between 2 and 5.

Using (2'E,7'R,11'R)-1-(2,5-dimethoxy-3,4,6-trimethylphenyl)-3,7,11,15-tetramethylhexadec-2-en-1-one (I-ERR) as starting material for the above oxidation, 2,3,5-trimethyl-6-((2'E,7'R,11'R)-3,7,11,15-tetramethylhexadec-2-enoyl)cyclohexa-2,5-diene-1,4-dione (III-ERR), as preferred embodiment of compound of formula (III), is formed.

(III-ERR)

Compound of formula (III) can be purified by suitable methods. Particularly useful are purification by extraction and/or chromatography using silica as stationary phase.

The starting product for this reaction, i.e. compound of formula (I), is preferably produced by a process as mentioned above [reaction a)].

In a further aspect, the present invention relates to a process of manufacturing a compound of formula (IV) from a compound of formula (III)

(IV)

(III)

by a dithionite anion or a dithionite salt, particularly by sodium dithionite or an aqueous solution thereof.

It is preferred that said reaction occurs in the presence of water, more preferably in the presence of water and an organic solvent, more preferably of water and a polar aprotic organic solvent, most preferably in the presence of water and tetrahydrofuran.

It is furthermore preferred, that the reaction takes place under an inert atmosphere, such as under nitrogen or under argon) and/or under exclusion of light.

It is preferred that the molar ratio of dithionite to compound of formula (III) is more than 1.2, preferably between 1.2 and 4, more preferably between 1.3 and 1.7.

This process is schematically shown in FIG. 1 as reaction b2).

The starting product for this reaction, i.e. compound of formula (III), is preferably produced by a process as mentioned above [reaction b1)].

Therefore, compound of formula (IV) can on the one hand be prepared in a two-step process from compound of formula (I) as shown above.

On the other hand, compound of formula (IV) an be prepared directly from compound of formula (I) by a process of manufacturing a compound of formula (IV) from a compound of formula (I)

(IV)

(I)

using BBr$_3$. The molar ratio of boron tribromide to the compound of formula (I) is preferably larger than 2, more preferably in the range of between 2 and 10, even more preferably between 2.1 and 3.5.

This process is preferably performed in a halogenated hydrocarbon, particularly in a halogenated hydrocarbon selected from the group consisting of chlorinated methane, ethane, propane, butane and pentane as well as their constitutional isomers. Preferably the halogenated hydrocarbons comprise more than 1 halogen atom. The most preferred organic solvent is dichloromethane.

The process is generally performed at a temperature of between 10° C. and 60° C., particularly at room temperature (23° C.).

Furthermore, it is advantageous, that the oxidation is performed in an organic solvent, preferably in a hydrocarbon, particularly an aliphatic hydrocarbon, preferably in an aliphatic hydrocarbon selected from the group consisting of pentane, hexane, heptane and cyclohexane, as well as their constitutional isomers, or in a halogenated hydrocarbon, particularly in a halogenated hydrocarbon selected from the group consisting of chlorinated methane, ethane, propane, butane and pentane as well as their constitutional isomers. Preferably the halogenated hydrocarbons comprise more than 1 halogen atom. Preferred halogenated hydrocarbon is dichloromethane. The hydrocarbons are preferred in comparison to the halogenated hydrocarbons.

Most preferred organic solvent is hexane.

Comparing the two pathways to compound of formula (IV) from compound of formula (I) shown above, i.e. the two-step reaction [b1) and b2)] via compound of formula (III), and the one-step reaction [b3)], in the one-step reaction isomerisation of the double bond to a higher degree can be observed. Therefore, when starting from the E-isomer of compound of formula (I) a mixture of E- and Z-isomers comprising a rather high amount of the Z-isomer of compound of formula (IV) is obtained. Therefore, it is preferred to use the two-step reaction [b1) and b2)] from compound of formula (I) to compound of formula (IV).

In a further aspect, the present invention relates to a process of manufacturing a compound of formula (V) from a compound of formula (IV)

(V)

(IV)

in a cyclization reaction using pyrrolidine or a 2-substituted pyrrolidine compound;

Pyrrolidine is the compound of formula (VIII-c)

(VIII-c)

Substituted pyrrolidines are pyrrolidines which carry a substituent at the carbon center in the 2-position of the pyrrolidine ring. This gives rise to a chirality center at the carbon next to the nitrogen atom in the pyrrolidine ring.

Suitable substituted pyrrolidines are particularly pyrrolidines which are substituted at the 2-position of the pyrrolidine ring.

2-Substituted pyrrolidine compounds are preferably compounds of formula (VIII)

(VIII)

wherein Y$^1$ represents either
a C$_{1-6}$ alkyl group or a group CH$_2$Y$^2$ or or a substituent carrying a Brønsted acid functional group;
wherein R$^6$ represents a linear or branched C$_{1-12}$-alkyl group which optionally further comprises at least one aromatic group and/or C=O and/or NH and/or NH$_2$ group;
Y$^2$ represents either OH or OR$^7$ or NHR$^7$ or NHCOOR$^7$ or wherein $R^7$ represents either
- a linear or branched $C_{1-12}$-alkyl group which optionally further comprises at least one aromatic group and/or C=O and/or NH and/or $NH_2$ group
or
- an aryl group or a substituted aryl group or a heteroaryl group or a substituted heteroaryl group

Figure 4:
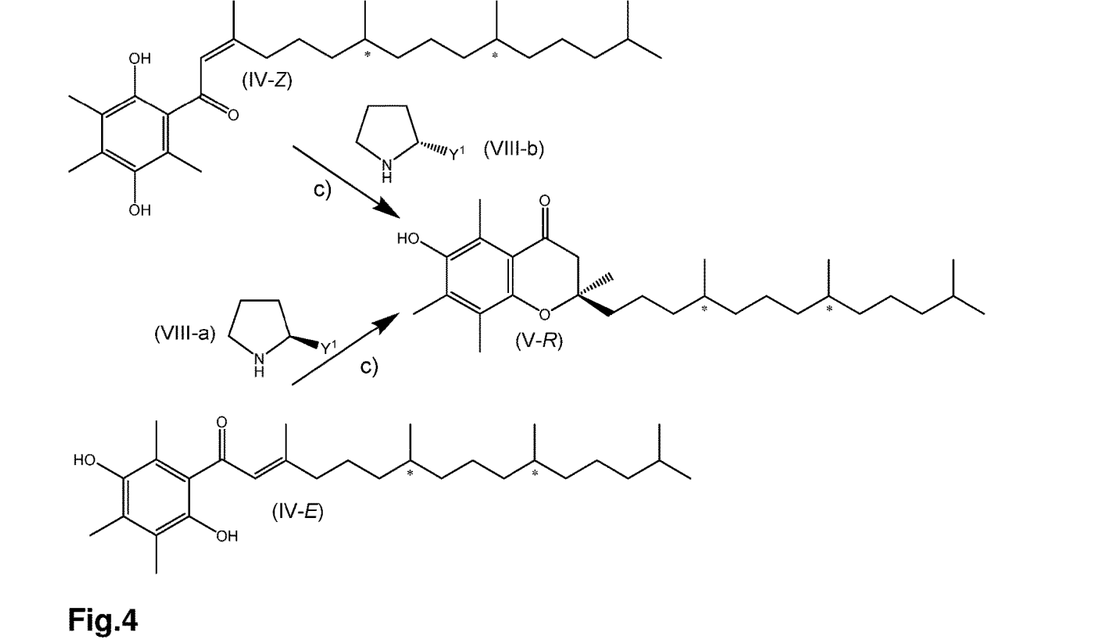
FIG. 4 schematically show synthesis processes for forming a compound of formula (V-R) from compounds of formulas (IV-Z) and (IV-E), respectively.

This process is schematically shown in FIG. 1, respectively in FIG. 4, as reaction c).

A preferred 2-substituted pyrrolidine compound of formula (VIII) having a substituent carrying a Brønsted acid functional group as $Y^1$ is particularly 1,1,1-trifluoro-N-(pyrrolidin-2-ylmethyl)methanesulfonamide.

Compounds of formula (VIII) have a chiral center in the 2-position of the pyrrolidine ring. We have observed that the configuration at this carbon center significantly influences the chirality at the carbon center marked by # in formula (V).

We have, furthermore, observed that if the compound of formula (IV) has the E-configuration at the C—C double bond (next to the wavy line) in formula (IV), i.e. of formula (IV-E), and the isomer of compound of formula (VIII-a) is used in said reaction c), the isomer of compound of formula (V) having the R-configuration (at the center marked by #), i.e. compound of formula (V-R), is predominantly formed.

(IV-E)

(VIII-a)

(V-R)

When the compound of formula (IV-ERR) is used in this reaction in using the isomer of compound of formula (VIII-a), accordingly predominately the compound of formula (V-RRR) is formed.

(IV-ERR)

(V-RRR)

In contrast, if the other isomer of compound of formula (VIII), i.e. (VIII-b), is used then the isomer of compound of formula (V) having the S-configuration (at the center marked by #), i.e. compound of formula (V-S), is predominantly formed.

(VIII-b)

(V-S)

When using the compound of formula (IV-ERR) in this reaction, accordingly the compound of formula (V-SRR) is predominantly prepared.

(V-SRR)

The predominant synthesis of either the R or S isomer of compound of formula (V) is very surprising and commercially interesting. The stereoselectivity can be optimised particularly by increase of the isomeric purity of the starting materials and intermediates.

Furthermore, the desired isomer of compound of formula (V) can be isolated by chromatographic techniques, such as disclosed in WO2012/152779 A1.

In a preferred embodiment, compound of formula (IV-E) is cyclized to the compound of formula (V-R) using (S)-1,1,1-trifluoro-N-(pyrrolidin-2-ylmethyl)-methanesulfonamide

When compound of formula (IV-Z) is used, it is cyclized in the presence of (R)-1,1,1-trifluoro-N-(pyrrolidin-2-ylmethyl)methanesulphonamide to the compound of formula (V-R).

Therefore, in another aspect, the invention relates to a process of stereoselectively manufacturing a compound of formula (V-R)

(V-R)

from a compound of formula (IV-E)

(IV-E)

in a cyclization reaction using a 2-substituted pyrrolidine compound of formula (VIII-a)

(VIII-a)

or from a compound of formula (IV-Z)

(IV-Z)

in a cyclization reaction using a 2-substituted pyrrolidine compound of formula (VIII-b)

(VIII-b)

wherein * represents a chiral center. Details have been described above in great detail and also illustrated by FIG. 4.

When on the other hand, pyrrolidine (VIII-c) (which is achiral) or a mixture of the chiral isomers of the formula (VIII-a) and of formula (VIII-b) is used for compound of formula of either (IV-E) or (IV-Z), the reaction product, i.e. formula (V), is an isomeric (2R/2S) mixture relative to the chiral center marked by # in formula (V).

(IV-E)

(IV-Z)

Accordingly, when using pyrrolidine (formula (VIII-c), either (IV-ERR) [being accessible from (E,R,R)-phytal, respectively from (E,R,R)-phytol)] or (IV-ZRR) [being accessible from (Z,R,R)-phytal, respectively from (Z,R,R)-phytol)], a racemic mixture having R and S configuration at the center marked by # in formula (V-RR) is obtained.

(IV-ERR)

(IV-ZRR)

-continued (V-RR)

The starting product for this reaction, i.e. compound of formula (IV), is preferably produced by a process as mentioned above [reaction b1) & b2) or b3)], more preferably by a the two-step reaction process [reaction b1) & b2)].

It is advantageous, that the cyclization is performed in an organic solvent, preferably in a hydrocarbon, particularly an aliphatic hydrocarbon, preferably in an aromatic hydrocarbon, preferably in toluene.

The cyclization is generally performed at a temperature of between 10° C. and the reflux temperature of the solvent used. It is further preferred that the reaction is performed in a first phase at a temperature of between 10° C. and 60° C., and in a second phase at a temperature of between 100° C. and 140° C.

The cyclization is preferably performed under inert atmosphere, such as nitrogen or argon.

The molar ratio of pyrrolidine or 2-substituted pyrrolidine compound to the compound of formula (IV) is preferably between 1.1 and 5, particularly between 1.3 and 2.

Compound of formula (V) can be purified by suitable methods. Particularly useful is purification by chromatography using silica as stationary phase and/or by extraction.

Compound of formula (V), preferably of formula (V-R), can be chemically transformed to compound of formula (VII), particularly of formula (VII-R) as shown schematically in FIG. 2, respectively in FIG. 2a

In one embodiment, the compound of formula (V), respectively (V-R), is chemically transformed by a two-step process, first from compound of formula (V) by reaction d1) to compound of formula (VI) followed by reaction d2), to compound of formula (VII), respectively (VII-R).

Reaction d1) is particularly a reduction of formula (V), respectively (V-R), by sodium boranate, followed by acid treatment, as disclosed by Kabbe and Heitzer, *Synthesis* 1978; (12): 888-889. Reaction d2) is also a reduction, i.e. a partial hydrogenation, particularly by sodium/ethanol such as described in Schudel, Mayer, Isler, *Helv. Chim. Acta* 46, 2517-2526 (1963), the whole disclosure of which is incorporated herein by reference.

In another embodiment, the compound of formula (V), respectively (V-R), is chemically transformed by a one-step process by reaction d3) to compound of formula (VII), respectively (VII-R). This reaction d3) is particularly made by the reaction of metallic zinc in the presence of an acid or an acid mixture, for example as disclosed for in U.S. Pat. No. 6,096,907, the whole disclosure of which is incorporated herein by reference.

Therefore, in a further aspect, the present invention relates to a process of manufacturing a compound of formula (VII) from a compound of formula (IV)
comprising the step
i) manufacturing a compound of formula (V) from a compound of formula (IV) as described in great detail above
followed either by a one-step reaction d3)
d3) chemically transforming the compound of formula (V) to the compound of formula (VII)
or by a two-step reaction of the sub-steps d1) and d2)
d1) chemically transforming the compound of formula (V) to a compound of formula (VI)
and
d2) chemically transforming the compound of formula (VI) to the compound of formula (VII)

Therefore, starting from compound of formula (V), (V-S), (V-R), (V-RR), V-SRR) and (V-RRR), the respective compounds of formula (VII), (VII-S), (VII-R), (VII-RR), (VII-SRR) and (VII-RRR) can be obtained, eventually by their respective intermediates of formula (VI), (VI-S), (VI-R), (VI-RR), (VI-SRR) and (VI-RRR)

(VII)

(VII-S)

(VII-R)

(VII-RR)

(VII-SRR)

(VII-RRR)

(VI)

-continued

(VI-S)

(VII-R)

comprising the step
i) manufacturing stereoselectively a compound of formula (V-R) according to a process according to claim 11

(VI-R)

(V-R)

(VI-RR)

followed either by a one-step reaction d3)
d3) chemically transforming the compound of formula (V-R) to the compound of formula (VII-R)
or by a two-step reaction of the sub-steps d1) and d2)
d1) chemically transforming the compound of formula (V-R) to a compound of formula (VI-R);

(VI-SRR)

(VI-R)

(VI-RRR)

and
d2) chemically transforming the compound of formula (VI-R) to the compound of formula (VII-R)
wherein * represent chiral centers.
Details for the individual steps have been described above in great detail.

In a further embodiment, the present invention relates to the novel compound of formula (I), particularly of formula (I-E)

Most preferred is, that (2R,4'R,8'R)-α-tocopherol (VII-RRR) can be prepared from (R)-2,5,7-trimethyl-2-((4R,8R)-4,8,12-trimethyltridecyl)-2H-chromen-6-ol (VI-RRR), respectively from (R)-6-hydroxy-2,5,7-trimethyl-2-((4R,8R)-4,8,12-trimethyltridecyl)chroman-4-one (V-RRR).

(V-RRR)

(I)

(VI-RRR)

(I-E)

Hence, in another aspect, the present invention relates to a process of manufacturing stereoselectively a compound of formula (VII-R) from a compound of formula (IV)

Details related to the formula, the possibilities of its synthesis, uses and preferred embodiments have been already described in detail above.

In a further embodiment, the present invention relates to the novel compound (III), particularly of formula (III-E)

(III)

(III-E)

Details related to the formula, the possibilities of its synthesis, uses and preferred embodiments have been already described in detail above.

In a further embodiment, the present invention relates to the novel compound (IV), particularly of formula (IV-E)

(IV)

(IV-E)

Details related to the formula, the possibilities of its synthesis, uses and preferred embodiments have been already described in detail above.

EXAMPLES

The present invention is further illustrated by the following experiments.

Synthesis of (2'E,7'R,11'R)-1-(2,5-dimethoxy-3,4,6-trimethylphenyl)-3,7,11,15-tetramethylhexadec-2-en-1-ol (II-ERR)

2.7 g magnesium has been added to tetrahydrofuran (THF) in a glass flask, fitted with argon supply, a dropping funnel, a reflux condenser and a magnetic stirring bar, and activated thereafter with 1,2-dibromoethane. Then 23.8 g 1-bromo-2,5-dimethoxy-3,4,6-trimethylbenzene (91.8 mmol, prepared from 1,4-dimethoxy-2,3,5-trimethylbenzene and $Br_2$) in 95 ml THF have been added dropwise and under stirring under argon. After stirring under refluxing temperature for 1.5 hour, the reaction mixture has been cooled to −5° C. To this mixture 20.8 g (E,R,R)-phytal (=(2'E,7'R,11'R)-3,7,11,15-tetramethylhexadec-2-enal) (70.6 mmol, prepared from (E,R,R)-phytol by oxidation with $MnO_2$ and purification by chromatography using silica) have been added dropwise and under stirring and cooling under argon. After gentle warming to room temperature, the reaction mixture was stirred for 1.5 hours. Thereafter, 20 ml of water have been slowly added under cooling to avoid extensive heating by the exothermic reaction. After filtration, the filtrate has been extracted with hexane. After drying and rotary evaporation at 40° C. of hexane 36.9 g of a yellow oil which has been purified by flash chromatography using silica and hexane/diethyl ether=19/1. After drying and evaporation of the solvent
(2'E,7'R,11'R)-1-(2,5-dimethoxy-3,4,6-trimethylphenyl)-3,7,11,15-tetra-methylhexadec-2-en-1-ol has been isolated and identified by $^1$H-NMR spectroscopy.

Synthesis of (2'E,7'R,11'R)-1-(2,5-dimethoxy-3,4,6-trimethylphenyl)-3,7,11,15-tetramethylhexadec-2-en-1-one (I-ERR)

14.2 g (2'E,7'R,11'R)-1-(2,5-dimethoxy-3,4,6-trimethylphenyl)-3,7,11,15-tetramethylhexadec-2-en-1-ol (29.9 mmol) have been added under argon to 250 ml hexane in a glass flask fitted with argon supply and a mechanical stirrer, 156 g precipitated (active) $MnO_2$ (1.79 mol) have been added under intense stirring in portions of about 30 g. When analysis by thin layer chromatography (TLC) ($SiO_2$, hexane/ethyl acetate=4/1) confirmed complete oxidation, the reaction mixture has been filtered. After evaporation of the hexane 15.2 g of a yellow crude product has been collected.

The crude product has been purified by flash chromatography using silica and hexane/ethyl acetate=19/1. After drying and evaporation of the solvent 11.4 g of (2'E,7'R,11'R)-1-(2,5-dimethoxy-3,4,6-trimethylphenyl)-3,7,11,15-tetramethyl-hexadec-2-en-1-one as a lemon-yellow oil has been isolated (80.9% yield)

Analysis by GC and LC have identified a E/Z ratio (i.e. (2'E,7'R,11'R)-1-(2,5-dimethoxy-3,4,6-trimethylphenyl)-3,7,11,15-tetramethylhexadec-2-en-1-one/(2'Z,7'R,11'R)-1-(2,5-dimethoxy-3,4,6-trimethylphenyl)-3,7,11,15-tetramethyl-hexa-dec-2-en-1-one) of 99.3/0.7.

The compound has been identified and characterized by $^1$H-NMR, $^{13}$C-NMR, IR, MS and microanalysis:

$^1$H NMR (300 MHz, $CDCl_3$): δ=6.27 (1H, d, J=1.1 Hz, 2'-H), 3.65 ($OCH_3$), 3.63 ($OCH_3$), 2.08-2.26 (12H, 4 $CH_3$), 0.96-1.63 (21H, m, 9 $CH_2$, 3 CH), 0.80-0.92 ppm (12H, m, 4 aliph. $CH_3$)

$^{13}$C NMR (75 MHz, $CDCl_3$): δ=196.8, 159.6, 153.1, 150.5, 135.9, 131.6, 128.7, 125.8, 125.1, 62.1, 60.1, 41.8, 39.4, 37.4, 37.3, 37.3, 36.6, 32.8, 32.6, 28.0, 25.0, 24.8, 24.4, 22.7, 22.6, 19.7, 19.6, 19.4, 12.9, 12.4, 12.3 ppm.

$C_{31}H_{52}O_3$ (472.75), calc. C, 78.76, H, 11.09, found C, 77.43, H, 11.06.

Synthesis of 2,3,5-trimethyl-6-((2'E,7'R,11'R)-3,7,11,15-tetramethylhexadec-2-enoyl)cyclohexa-2,5-diene-1,4-dione (III-ERR)

5.9 g (2'E,7'R,11'R)-1-(2,5-dimethoxy-3,4,6-trimethylphenyl)-3,7,11,15-tetramethylhexadec-2-en-1-one (12.5 mmol) have been put under exclusion of light in 35 ml toluene and 70 ml glacial acetic acid at 0° C. To this a solution of 14.6 g $Ce(NH_4)_2(NO_3)_6$ in 75 ml glacial acetic acid, 25 ml acetonitrile and 17 ml water have been added dropwise under argon and under exclusion of light. The orange slightly turbid reaction mixture was continued to be stirred at 0° C. to complete the reaction. After warming up to room temperature the reaction mixture was poured onto 200 ml water and extracted by means of hexane. After washing the organic phase with water and a solution of saturated NaHCO$_3$ the organic phase has been dried. After removal of the hexane at reduced pressure and under exclusion of light 7.0 g of an orange oil have been obtained which then has been purified by flash chromatography using silica and hexane/diethyl ether=19/1. After drying and evaporation of the solvent 3.61 g of 2,3,5-trimethyl-6-((2'E,7'R,11'R)-3,7,11,15-tetramethylhexadec-2-enoyl)cyclohexa-2,5-diene-1,4-dione as an orange oil has been isolated and identified (65.4% yield).

Analysis by LC has identified a E/Z ratio (i.e. 2,3,5-trimethyl-6-((2'E,7'R,11'R)-3,7,11,15-tetramethylhexadec-2-enoyl)cyclohexa-2,5-diene-1,4-dione/2,3,5-trimethyl-6-((2'Z,7'R,11'R)-3,7,11,15-tetramethylhexadec-2-enoyl)cyclohexa-2,5-diene-1,4-dione, of 98.06/1.94.

The compound has been identified and characterized by $^1$H-NMR, $^{13}$C-NMR, IR, MS and microanalysis:

$^1$H NMR (300 MHz, CDCl$_3$): δ=6.06-6.11 (1H, m, 2'-H, E+Z), 2.09-2.27 (5H, m, 3'-CH$_3$, 4'-CH$_2$), 1.90-2.08 (9H, m, 3 CH$_3$), 0.95-1.60 (19H, m, 8 CH$_2$, 3 CH), 0.80-0.90 ppm (12H, m, 4 aliph. CH$_3$.

$^{13}$C NMR (75 MHz, CDCl$_3$): δ=192.2, 187.8 (2C), 163.2, 143.8, 141.0, 140.2, 139.5, 123.3, 41.9, 39.4, 37.4, 37.3, 36.6, 32.8, 32.6, 28.0, 24.9, 24.8, 24.4, 22.7, 22.6, 20.1, 19.7, 19.6, 12.6, 12.5, 12.0 ppm.

C$_{29}$H$_{46}$O$_3$ (442.68), calc. C, 78.68, H, 10.47, found C, 78.92, H, 10.56.

Synthesis of (2'E,7'R,11'R)-1-(2,5-dihydroxy-3,4,6-trimethylphenyl)-3,7,11,15-tetramethylhexadec-2-en-1-on (IV-ERR)

All solvents were saturated with argon before usage.
2,3,5-trimethyl-6-((2'E,7'R,11'R)-3,7,11,15-tetramethyl-hexadec-2-enoyl)cyclohexa-2,5-diene-1,4-dione (0.25 g, 0.48 mmol) was dissolved in tetrahydrofuran (2.0 ml) and stirred under argon and exclusion of light at 21° C. Sodium dithionite (0.15 g, 0.72 mmol, 1.5 eq., 85%) in water (1.44 ml) was added dropwise over 3 minutes. After 4 h stirring at 21° C. the reaction mixture was extracted three times with dichloromethane (3×10 ml) under argon. The combined organic extracts were washed once with water (10 ml) and evaporated at 40° C./500 to ca.30 mbar to give 289.4 mg orange oil which was identified to be (2'E,7'R,11'R)-1-(2,5-dihydroxy-3,4,6-trimethylphenyl)-3,7,11,15-tetramethyl-hexadec-2-en-1-on. The compound has been characterized by $^1$H-NMR and $^{13}$C-NMR.

$^1$H NMR (300 MHz, CDCl$_3$): δ=10.82-10.87 (1H, m, 2-OH), 6.313 (q, $^4$J=1.13 Hz, E-isomer) and 6.275 (q, $^4$J=1.13 Hz, Z-isomer) (1H, 2'-H), 4.34 (1H, br.s, 5-OH), 1.93-2.63 (14H, m, 4'-H, 4 CH$_3$; $^4$J=1.13 Hz coupling also seen in the doublet of the methyl groups at 2.19 ppm), 0.95-1.69 (19H, m, 8 CH$_2$, 3 CH), 0.77-0.93 ppm (12H, m, 4 aliph. CH$_3$); E/Z ratio 79:21.

$^{13}$C NMR (75 MHz, CDCl$_3$): δ=197.8, 159.1, 152.4, 144.9, 130.1, 127.3, 126.5, 123.3, 118.6, 41.7, 39.4, 37.4, 37.3, 36.7; 32.8, 32.7, 28.0, 25.6, 24.9, 24.8, 24.4, 22.7, 22.6, 19.7, 19.6, 15.6, 13.0, 11.8 ppm.

Synthesis of (S)-6-hydroxy-2,5,7-trimethyl-2-((4R,8R)-4,8,12-trimethyltridecyl)chroman-4-one (V-SRR)

303.6 mg (2'E,7'R,11'R)-1-(2,5-dihydroxy-3,4,6-trimethylphenyl)-3,7,11,15-tetramethylhexadec-2-en-1-on (500 μmol) are dissolved in 1.6 mL toluene in a 25 mL round bottom flask, fitted with argon supply, a reflux condenser and a magnetic stirring bar. 188 mg (R)-1,1,1-trifluoro-N-(pyrrolidin-2-ylmethyl)methanesulfonamide (800 μmol, 1.58 equiv.) is added leading to a yellow suspension. The reaction mixture is stirred for 17 hours at 23° C. and is then heated to reflux (110° C.). The reaction mixture is stirred for two hours at 110° C., the eliminated water is trapped in the Dean-Stark trap. Then the mixture is cooled to 23° C. Hydrochloric acid (2 N, 3 mL) and water (10 mL) are added, leading to a yellow-brownish suspension. The toluene layer is washed three times with 10 mL water each. The combined aqueous phases are extracted three times with 10 mL dichloromethane each. The combined organic layers are dried over Na$_2$SO$_4$ and concentrated under reduced pressure (40° C., 10 mbar). The crude product is obtained in 296.9 mg containing 23% by weight (153 μmol, 31% yield) of the desired chromanone. Chiral HPLC revealed a diastereomeric ratio of the 2R-isomer:2S isomer of 40:60 (ee=20%).

$^1$H NMR (CDCl$_3$, 300 MHz): δ=4.64 (s, 1H), 2.70 (dd, J=1.32 Hz, J=15.82, 1H), 2.60 (dd, J=0.75 Hz, J=15.82, 1H), 2.55 (s, 3H), 1.35 (s, 3H), 0.97-1.81 (m, 26H), 0.86-0.91 (m, 4H), 0.85 (s, 6H), 0.82 ppm (s, 3H).

$^{13}$C NMR (CDCl$_3$, 75 MHz): δ=195.5, 195.5, 153.0, 145.8, 132.3, 131.0, 123.9, 123.4, 120.6, 116.7, 79.6, 77.5, 77.2, 77.1, 76.6, 49.5, 49.5, 44.2, 39.7, 39.6, 39.4, 37.4, 37.3, 37.1, 36.6, 32.8, 32.7, 32.6, 29.9, 28.0, 24.8, 24.4, 23.7, 23.7, 22.7, 22.6, 21.5, 21.0, 19.8, 19.7, 19.6, 19.6, 19.5, 13.4, 12.9, 12.0 ppm.

Synthesis of (R)-6-hydroxy-2,5,7-trimethyl-2-((4R, 8R)-4,8,12-trimethyltridecyl)chroman-4-one (V-RRR)

Using (S)-1,1,1-trifluoro-N-(pyrrolidin-2-ylmethyl)methanesulfonamide analogously in the above synthesis, (R)-6-hydroxy-2,5,7-trimethyl-2-((4R,8R)-4,8,12-trimethyltridecyl)chroman-4-one (V-RRR) is formed predominantly.

Synthesis of a diastereomeric mixture of (2RS)-6-hydroxy-2,5,7-trimethyl-2-((4R,8R)-4,8,12-trimethyltridecyl)chroman-4-one (V-RRR)/(V-SRR)

108.9 mg (2'E,7'R,11'R)-1-(2,5-dihydroxy-3,4,6-trimethylphenyl)-3,7,11,15-tetramethylhexadec-2-en-1-on (243 μmol) is dissolved in 0.7 mL toluene. Then 0.027 mL pyrrolidine (23 mg, 329 μmol, 1.37 equiv.) are added. The orange solution is stirred for 16 hours at 23° C., leading to a dark red solution. Then 15 mL toluene are added and the reaction mixture is heated to 120° C. for 2 h while water is trapped in the Dean-Stark trap. Then the mixture is cooled to 23° C. and 1 mL 2 N HCl and 5 mL water are added, leading to an orange brown suspension. The toluene phase is extracted three times with water (5 mL each). The combined aqueous phases are extracted three times with dichloromethane (5 mL each, total 15 mL). The combined organic phases are dried over sodium sulfate, concentrated under reduced pressure (40° C., max. 10 mbar) and analyzed by HPLC and NMR.

The reaction product has been identified as a 2RS isomeric mixture of (R)-6-hydroxy-2,5,7-trimethyl-2-((4R, 8R)-4,8,12-trimethyltridecyl)chroman-4-one and (S)-6-hydroxy-2,5,7-trimethyl-2-((4R,8R)-4,8,12-trimethyltridecyl)chroman-4-one. Yield 77.5% (105.3 mg, 183 μmol).

Synthesis of (2R,4'R,8'R)-α-tocopherol (R)-6-hydroxy-2,5,7-trimethyl-2-((4R,8R)-4,8,12-trimethyltridecyl)chroman-4-one (V-RRR) was transformed to

(2R,4'R,8'R)-α-tocopherol by treatment with zinc dust and aqueous hydrochloric acid, as described by Baldenius et al., EP 0 989 126 A1. The compound obtained showed identical retention time in comparison to an authentic sample of α-tocopherol, and the values obtained by measuring the $^1$H NMR (CDCl$_3$, 300 MHz) were identical with the values for α-tocopherol, as for example reported by J. K. Baker and C. W. Myers, *Pharmaceutical Research* 1991, 8, 763-770.

Synthesis of (2RS,4'R,8'R)-α-tocopherol

In analogy to the example given above, (2RS)-6-hydroxy-2,5,7,8-tetramethyl-2-(4,8,12-trimethyltridecyl)chroman-4-one was transformed to (2RS,4'R,8'R)-α-tocopherol by treatment with zinc dust and aqueous hydrochloric acid, as described by Baldenius et al., EP 0 989 126 A1.

The invention claimed is:

1. A process of manufacturing stereoselectively a compound of formula (IV):

wherein the process comprises subjecting a compound of formula (I):

to a two-step chemical reaction comprising the substeps of:

(1) subjecting the compound of formula (I) to an oxidative demethylation reaction to form a compound of formula (III):

and then subsequently (2) reacting the compound of formula (III) with a dithionite compound or a salt thereof to form the compound of formula (IV), wherein * represent chiral centers.

2. The process according to claim 1, wherein the substep (2) comprises reacting the compound of formula (III) with a sodium dithionite or an aqueous solution thereof.

3. The process according to claim 1, wherein the substep (2) occurs in the presence of water.

4. The process according to claim 1, wherein the substep (2) occurs in the presence of water and an organic solvent.

5. The process according to claim 4, wherein the organic solvent is a polar aprotic organic solvent.

6. The process according to claim 5, wherein the polar aprotic organic solvent comprises tetrahydrofuran.

7. The process according to claim 1, wherein the substep (2) is conducted under an inert atmosphere and/or under exclusion of light.

8. The process according to claim 1, wherein a molar ratio of the dithionite compound or salt thereof to the compound of formula (III) is more than 1.2.

9. The process according to claim 8, wherein the molar ratio of the dithionite compound or salt thereof to the compound of formula (III) is between 1.2 and 4.

10. The process according to claim 8, wherein the molar ratio of the dithionite compound or salt thereof to the compound of formula (III) is between 1.3 and 1.7.

* * * * *